(12) United States Patent
Iddan

(10) Patent No.: US 7,866,322 B2
(45) Date of Patent: Jan. 11, 2011

(54) DEVICE, SYSTEM AND METHOD FOR TRANSFER OF SIGNALS TO A MOVING DEVICE

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1359 days.

(21) Appl. No.: 10/531,378

(22) PCT Filed: Oct. 15, 2003

(86) PCT No.: PCT/IL03/00834

§ 371 (c)(1),
(2), (4) Date: Feb. 23, 2006

(87) PCT Pub. No.: WO2004/036803

PCT Pub. Date: Apr. 29, 2004

(65) Prior Publication Data

US 2006/0169292 A1    Aug. 3, 2006

Related U.S. Application Data

(60) Provisional application No. 60/418,162, filed on Oct. 15, 2002.

(51) Int. Cl.
*A61B 19/00* (2006.01)
(52) U.S. Cl. ...................................................... 128/899
(58) Field of Classification Search ................. 128/899; 600/300–302, 309, 424, 549
See application file for complete search history.

(56) References Cited

U.S. PATENT DOCUMENTS

| | | |
|---|---|---|
| 3,322,374 A | 5/1967 | King, Jr. et al. |
| 3,683,389 A | 8/1972 | Hollis |
| 3,683,890 A | 8/1972 | Beal |
| 3,723,644 A | 3/1973 | Haskell et al. |
| 3,971,362 A | 7/1976 | Pope et al. |
| 4,109,644 A | 8/1978 | Kojima |
| 4,149,769 A | 4/1979 | Zobel |
| 4,178,735 A | 12/1979 | Jackson |
| 4,180,736 A | 12/1979 | Goodman |
| 4,198,960 A | 4/1980 | Utsugi |
| 4,239,040 A | 12/1980 | Hosoya et al. |

(Continued)

FOREIGN PATENT DOCUMENTS

DE    2929429    2/1980

(Continued)

OTHER PUBLICATIONS

Japanese Office Action of Japanese Application No. 2004-544663 mailed on Dec. 22, 2009.

(Continued)

*Primary Examiner*—John P Lacyk
(74) *Attorney, Agent, or Firm*—Pearl Cohen Zedek Latzer, LLP

(57) ABSTRACT

A system for transfer of a signal, such as an energizing signal, to a transmitting in vivo sensing device. The in vivo device includes at least one signal transmitter and at least one signal receiving unit. The system includes an external phased array antenna. The phased array antenna receives a signal from the sensing device and then transmits a signal to the device phased in the reverse order to that of receipt the signal from the sensing device.

18 Claims, 6 Drawing Sheets

U.S. PATENT DOCUMENTS

| | | |
|---|---|---|
| 4,246,792 A | 1/1981 | Matzuk |
| 4,262,632 A | 4/1981 | Hanton et al. |
| 4,278,077 A | 7/1981 | Mizumoto |
| 4,431,005 A | 2/1984 | McCormick |
| 4,439,197 A | 3/1984 | Honda et al. |
| 4,642,678 A | 2/1987 | Cok |
| 4,646,724 A | 3/1987 | Sato et al. |
| 4,689,621 A | 8/1987 | Kleinberg |
| 4,741,327 A | 5/1988 | Yabe |
| 4,803,992 A | 2/1989 | Lemelson |
| 4,819,620 A | 4/1989 | Okutsu |
| 4,844,076 A | 7/1989 | Lesho et al. |
| 4,854,328 A | 8/1989 | Pollack |
| 4,936,823 A | 6/1990 | Colvin et al. |
| 4,940,997 A | 7/1990 | Hamlin et al. |
| 5,042,486 A | 8/1991 | Pfeiler et al. |
| 5,081,041 A | 1/1992 | Yafuso et al. |
| 5,098,426 A | 3/1992 | Sklar et al. |
| 5,109,870 A | 5/1992 | Silny et al. |
| 5,187,572 A | 2/1993 | Nakamura et al. |
| 5,209,220 A | 5/1993 | Hiyama et al. |
| 5,211,165 A | 5/1993 | Dumoulin et al. |
| 5,217,449 A | 6/1993 | Yuda et al. |
| 5,239,418 A | 8/1993 | Tyler et al. |
| 5,262,871 A | 11/1993 | Wilder et al. |
| 5,267,033 A | 11/1993 | Hoshino |
| 5,279,607 A | 1/1994 | Schentag et al. |
| 5,330,427 A | 7/1994 | Weissenburger |
| 5,331,551 A | 7/1994 | Tsuruoka et al. |
| 5,337,732 A | 8/1994 | Grundfest et al. |
| 5,368,027 A | 11/1994 | Lubbers et al. |
| 5,373,322 A | 12/1994 | Laroche et al. |
| 5,373,840 A | 12/1994 | Knighton |
| 5,379,757 A | 1/1995 | Hiyama et al. |
| 5,382,976 A | 1/1995 | Hibbard |
| 5,395,366 A | 3/1995 | D'Andrea et al. |
| 5,398,670 A | 3/1995 | Ortiz et al. |
| 5,429,132 A | 7/1995 | Guy et al. |
| 5,441,041 A | 8/1995 | Sauer et al. |
| 5,452,004 A | 9/1995 | Roberts |
| 5,479,935 A | 1/1996 | Essen-Moller |
| 5,495,114 A | 2/1996 | Adair |
| 5,506,619 A | 4/1996 | Adams, Jr. et al. |
| 5,515,853 A | 5/1996 | Smith et al. |
| 5,549,109 A | 8/1996 | Samson et al. |
| 5,551,947 A | 9/1996 | Kaali |
| 5,558,640 A | 9/1996 | Pfeiler et al. |
| 5,569,292 A | 10/1996 | Scwemberger et al. |
| 5,572,252 A | 11/1996 | Naka et al. |
| 5,596,366 A | 1/1997 | Takashima et al. |
| 5,604,531 A | 2/1997 | Iddan et al. |
| 5,607,435 A | 3/1997 | Sachdeva et al. |
| 4,027,510 A | 6/1997 | Hiltebrandt |
| 5,642,353 A | 6/1997 | Roy, III et al. |
| 5,643,175 A | 7/1997 | Adair |
| 5,652,621 A | 7/1997 | Adams, Jr. et al. |
| 5,653,677 A | 8/1997 | Okada et al. |
| 5,666,955 A | 9/1997 | Kondo et al. |
| 5,681,260 A | 10/1997 | Ueda et al. |
| 5,681,279 A | 10/1997 | Roper et al. |
| 5,697,377 A | 12/1997 | Wittkampf |
| 5,697,384 A | 12/1997 | Miyawaki et al. |
| 5,738,110 A | 4/1998 | Beal et al. |
| 5,747,996 A | 5/1998 | Fuchs |
| 5,800,350 A | 9/1998 | Coppleson et al. |
| 5,819,736 A | 10/1998 | Avny et al. |
| 5,833,603 A | 11/1998 | Kovacs et al. |
| 5,837,196 A | 11/1998 | Pinkel et al. |
| 5,853,005 A | 12/1998 | Scanlon |
| 5,913,820 A | 6/1999 | Bladen et al. |
| 5,928,159 A | 7/1999 | Eggers et al. |
| 5,929,901 A | 7/1999 | Adair et al. |
| 5,986,693 A | 11/1999 | Adair et al. |
| 5,993,378 A | 11/1999 | Lemelson |
| 6,020,850 A | 2/2000 | Kyoto et al. |
| 6,043,839 A | 3/2000 | Adair et al. |
| 6,053,873 A | 4/2000 | Govari et al. |
| 6,074,349 A | 6/2000 | Crowley |
| 6,099,482 A | 8/2000 | Brune et al. |
| 6,149,581 A | 11/2000 | Klingenstein |
| 6,157,853 A | 12/2000 | Blume et al. |
| 6,165,128 A | 12/2000 | Céspedes et al. |
| 6,172,712 B1 | 1/2001 | Beard |
| 6,174,291 B1 | 1/2001 | McMahon |
| 6,184,922 B1 | 2/2001 | Saito et al. |
| 6,188,355 B1 | 2/2001 | Gilboa |
| 6,228,030 B1 | 5/2001 | Urbano et al. |
| 6,228,048 B1 | 5/2001 | Robbins |
| 6,229,578 B1 | 5/2001 | Acharya et al. |
| 6,233,476 B1 | 5/2001 | Strommer et al. |
| 6,240,312 B1 | 5/2001 | Alfano et al. |
| 6,254,548 B1 * | 7/2001 | Ishikawa et al. ............ 600/549 |
| 6,285,897 B1 | 9/2001 | Kilcoyne et al. |
| 6,304,769 B1 | 10/2001 | Arenson et al. |
| 6,324,418 B1 | 11/2001 | Crowley et al. |
| 6,366,186 B1 | 4/2002 | Hill et al. |
| 6,369,812 B1 | 4/2002 | Lyriboz et al. |
| 6,395,562 B1 | 5/2002 | Hammock et al. |
| 6,428,469 B1 | 8/2002 | Iddan et al. |
| 6,438,405 B1 | 8/2002 | Mooney et al. |
| 6,475,145 B1 | 11/2002 | Baylor |
| 6,488,694 B1 | 12/2002 | Lau et al. |
| 6,546,276 B1 | 4/2003 | Zanelli |
| 6,584,348 B2 | 6/2003 | Glukhovsky |
| 6,587,711 B1 | 7/2003 | Alfano et al. |
| 6,607,301 B1 | 8/2003 | Glukhovsky et al. |
| 6,632,175 B1 * | 10/2003 | Marshall ..................... 600/309 |
| 6,635,834 B1 | 10/2003 | Wenner |
| 6,689,056 B1 * | 2/2004 | Kilcoyne et al. ............ 600/300 |
| 6,690,963 B2 * | 2/2004 | Ben-Haim et al. .......... 600/424 |
| 6,692,430 B2 | 2/2004 | Adler |
| 6,709,387 B1 | 3/2004 | Glukhovsky et al. |
| 6,744,974 B2 | 6/2004 | Neuman |
| 6,764,440 B2 | 7/2004 | Iddan et al. |
| 6,934,573 B1 | 8/2005 | Glukhovsky et al. |
| 2001/0017649 A1 | 8/2001 | Yaron |
| 2001/0025135 A1 | 9/2001 | Naito et al. |
| 2001/0035902 A1 | 11/2001 | Iddan et al. |
| 2001/0051766 A1 | 12/2001 | Gazdzinski |
| 2002/0015952 A1 | 2/2002 | Anderson et al. |
| 2002/0032366 A1 | 3/2002 | Iddan et al. |
| 2002/0042562 A1 | 4/2002 | Meron et al. |
| 2002/0080881 A1 | 6/2002 | Honda et al. |
| 2002/0095187 A1 | 7/2002 | Thompson et al. |
| 2002/0103417 A1 | 8/2002 | Gazdzinski |
| 2002/0103425 A1 | 8/2002 | Mault |
| 2002/0146368 A1 | 10/2002 | Meron et al. |
| 2002/0158976 A1 | 10/2002 | Vni et al. |
| 2002/0165592 A1 | 11/2002 | Glukhovsky et al. |
| 2002/0173718 A1 | 11/2002 | Frisch et al. |
| 2002/0177779 A1 | 11/2002 | Adler et al. |
| 2002/0191113 A1 | 12/2002 | Siefken |
| 2002/0198439 A1 | 12/2002 | Mizuno |
| 2003/0013370 A1 | 1/2003 | Glukhovsky |
| 2003/0018280 A1 | 1/2003 | Lewkowicz et al. |
| 2003/0020810 A1 | 1/2003 | Takizawa et al. |
| 2003/0023150 A1 | 1/2003 | Yokoi et al. |
| 2003/0114742 A1 | 1/2003 | Lewkowicz et al. |
| 2003/0028078 A1 | 2/2003 | Glukhovsky |
| 2003/0040685 A1 | 2/2003 | Lewkowicz et al. |
| 2003/0043263 A1 | 3/2003 | Glukhovsky et al. |
| 2003/0045790 A1 | 3/2003 | Lewkowicz et al. |
| 2003/0060734 A1 | 3/2003 | Yokoi et al. |
| 2003/0077223 A1 | 4/2003 | Glukhovsky et al. |

| | | | |
|---|---|---|---|
| 2003/0085994 A1 | 5/2003 | Fujita et al. | |
| 2003/0117491 A1 | 6/2003 | Avni et al. | |
| 2003/0151661 A1 | 8/2003 | Davidson et al. | |
| 2003/0158503 A1 | 8/2003 | Matsumoto | |
| 2003/0167000 A1 | 9/2003 | Mullick et al. | |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0181788 A1 | 9/2003 | Yokoi et al. | |
| 2003/0195400 A1 | 10/2003 | Glukhovsky | |
| 2003/0195415 A1 | 10/2003 | Iddan | |
| 2003/0208107 A1 | 11/2003 | Refael | |
| 2003/0213495 A1 | 11/2003 | Fujita et al. | |
| 2003/0214579 A1 | 11/2003 | Iddan | |
| 2003/0214580 A1 | 11/2003 | Iddan | |
| 2003/0216622 A1 | 11/2003 | Meron et al. | |
| 2003/0229268 A1 | 12/2003 | Uchiyama et al. | |
| 2004/0027459 A1 | 2/2004 | Segawa et al. | |
| 2004/0027500 A1 | 2/2004 | Davidson et al. | |
| 2004/0073087 A1 | 4/2004 | Glukhovsky et al. | |
| 2004/0087832 A1 | 5/2004 | Glukhovsky et al. | |
| 2004/0109488 A1 | 6/2004 | Glukhovsky et al. | |
| 2004/0176664 A1 | 9/2004 | Iddan | |
| 2004/0215059 A1 | 10/2004 | Homan et al. | |
| 2004/0254455 A1 | 10/2004 | Iddan | |
| 2004/0225190 A1 | 11/2004 | Kimoto et al. | |
| 2004/0236182 A1 | 11/2004 | Iddan et al. | |
| 2004/0242962 A1 | 12/2004 | Uchiyama | |
| 2004/0258328 A1 | 12/2004 | Adler | |
| 2005/0025368 A1 | 2/2005 | Glukhovsky | |
| 2005/0110881 A1 | 5/2005 | Glukhovsky et al. | |
| 2005/0159643 A1 | 7/2005 | Zinaty et al. | |
| 2005/0222490 A1 | 10/2005 | Glukhovsky et al. | |

FOREIGN PATENT DOCUMENTS

| | | |
|---|---|---|
| DE | 29 41 363 | 4/1981 |
| DE | 34 40 177 | 6/1986 |
| DE | 19723454 | 12/1998 |
| EP | 0 667 115 | 8/1995 |
| EP | 00677272 | 10/1995 |
| FR | 2 688 997 | 10/1993 |
| IL | 126727 | 10/1998 |
| IL | 143258 | 5/2001 |
| IL | 143259 | 5/2001 |
| IL | 122602 | 4/2005 |
| JP | 5745833 | 3/1982 |
| JP | 3289779 | 12/1991 |
| JP | 4109927 | 4/1992 |
| JP | 1992-144533 | 5/1992 |
| JP | 4180736 | 6/1992 |
| JP | 5015515 | 1/1993 |
| JP | H-06-070902 | 3/1994 |
| JP | 6114037 | 4/1994 |
| JP | 6114064 | 4/1994 |
| JP | 6154191 | 6/1994 |
| JP | 6285044 | 10/1994 |
| JP | 7111985 | 5/1995 |
| JP | H-07-505017 | 6/1995 |
| JP | 7275197 | 10/1995 |
| JP | 7289504 | 11/1995 |
| JP | H10-065434 | 3/1998 |
| JP | 10243286 | 9/1998 |
| JP | H11-030659 | 2/1999 |
| JP | 2000-004115 | 1/2000 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001224553 | 8/2001 |
| JP | 2001231744 | 8/2001 |
| JP | 2001245844 | 9/2001 |
| JP | 2002000556 | 1/2002 |
| JP | 2002010990 | 1/2002 |
| JP | 2000342524 | 6/2002 |
| JP | 2000342525 | 6/2002 |
| WO | WO 92-21307 | 12/1992 |
| WO | WO 94-11040 | 5/1994 |
| WO | WO 98-11816 | 3/1998 |
| WO | WO 99-30610 | 6/1999 |
| WO | WO 99-32028 | 7/1999 |
| WO | WO 00-10456 | 3/2000 |
| WO | WO 00-22975 | 4/2000 |
| WO | WO 01-06917 | 2/2001 |
| WO | WO 01-8548 | 2/2001 |
| WO | WO 01-10291 | 2/2001 |
| WO | WO 01-35813 | 5/2001 |
| WO | WO 01-50941 | 7/2001 |
| WO | WO 01-65995 | 9/2001 |
| WO | WO 01-69212 | 9/2001 |
| WO | WO 01-87377 | 11/2001 |
| WO | WO 02-055126 | 7/2002 |
| WO | WO 02-055984 | 7/2002 |
| WO | WO 02-067593 | 8/2002 |
| WO | WO 02-073507 | 9/2002 |
| WO | WO 02-094337 | 11/2002 |
| WO | WO 02-095351 | 11/2002 |
| WO | WO 02-102224 | 12/2002 |
| WO | WO 03-003706 | 1/2003 |
| WO | WO 03-010967 | 2/2003 |
| WO | WO 03-011103 | 2/2003 |
| WO | WO 03-028224 | 4/2003 |
| WO | WO 03-094723 | 11/2003 |
| WO | WO 2004-004540 | 1/2004 |
| WO | WO 2004-028335 | 4/2004 |
| WO | WO 2004-028336 | 4/2004 |
| WO | WO 2004-035106 | 4/2004 |
| WO | WO 2004-036803 | 4/2004 |
| WO | WO 2004-045395 | 6/2004 |
| WO | WO 2004-054430 | 7/2004 |
| WO | WO 2004-088448 | 10/2004 |

OTHER PUBLICATIONS

U.S. Appl. No. 09/807,892, filed Jun. 6, 2001, Meron et al.
U.S. Appl. No. 10/130,326, filed May 15, 2002, Meron et al.
U.S. Appl. No. 10/166,025, filed Jun. 11, 2002, Lewkowicz et al.
U.S. Appl. No. 10/213,345, filed Aug. 7, 2002, Glukhovsky.
U.S. Appl. No. 10/493,751, filed Apr. 27, 2004, Glukhovsky et al.
U.S. Appl. No. 10/724,109, filed Dec. 1, 2003, Glukhovsky et al.
U.S. Appl. No. 60/306,872, filed Jul. 23, 2001, Glukhovsky et al.
U.S. Appl. No. 60/307,605, filed Jul. 26, 2001, Glukhovsky et al.
U.S. Appl. No. 60/324,067, filed Sep. 24, 2001, Lewkowicz et al.
U.S. Appl. No. 60/433,586, filed Dec. 16, 2002, Glukhovsky et al.
U.S. Appl. No. 60/457,592, filed Mar. 27, 2003, Iddan.
U.S. Appl. No. 60/482,456, filed Jun. 26, 2003, Glukhovsky.
BBC News Online—Pill camera to 'broadcast from the gut', Feb. 21, 2000, www.news.bbc.co.uk, printed Oct. 22, 2002.
"Bio-Medical Telemetry: Sensing and Transmitting Biological Information from Animals and Man", R. Stuart Mackay, John Wiley and Sons, New York, 1970, pp. 244-245.
"Color plane interpolation using alternating projections", B. Guntruck, Y. Altunbasak and R. Mersereau, IEEE Transactions on Image Processing, vol. 11, pp. 997-1013, 2002.

"Demosaicing: Image reconstruction from color ccd samples", R. Kimmel, IEEE Transactions on Image Processing, vol. 8, pp. 1221-1228, 1999.

"Estimating Motion in Image Sequences", Stiller et al., IEEE Signal Processing Magazine, Jul. 1999, pp. 70-91.

Evaluation of the Heidelberg PH Capsule: Method of Tubeless Gastric Analysis, Yarbrough, III et al., The American Journal Of Surgery, vol. 117, Feb. 1969, pp. 185-192.

Heidelberger Kapsel—ein Kleinstsender fur die pH-Messung im Magen, Lange, et al., Telefunken-Zeitung, Jg 36 (1963) Heft 5, pp. 265-270.

"Image Data Compression: A Review" Proceedings of the IEEE, IEEE, Jain A.K., New York, US, vol. 69, No. 3, Mar. 1, 1981, pp. 349-389.

"In Pursuit of the Ultimate Lamp", Craford et al., Scientific American, Feb. 2001.

International Search Report of PCT/IL02/00391, dated May 19, 2003.

International Search Report for PCT/IL99/0554 dated Apr. 4 2000.

International Search Report for PCT/IL2004/000287 dated Mar. 16, 2005.

International Search Report for PCT/IL02/00621 dated Dec. 6, 2002.

International Search Report for PCT/IL03/01080 filing date: Dec. 16, 2003.

International Search Report for PCT/IL01/00427 dated Sep. 19, 2002.

International Search Report for PCT/IL04/000280 Dated Oct. 25, 2004.

"Isfet Applications in Biological Matter: An Overview", F. Vald's-Perezgasga, et al., downloaded Oct. 27, 2002, www.cinstrum.unam.mx/revista/pdfv4n3/art3.PDF.

Katgraber F, Glenewinkel F, Fischler S, Int J. Legal Med 1998; 111(3) 154-6.

"Magnetic marker monitoring of disintegrating capsules", Weitschies, et al., European Journal of Pharmaceutical Sciences 13, 411-416, 2001.

Manual of Photogrammetry, Thompson (Ed.), Third Edition, vol. Two, Copyright 1944, 1952, 1966 by the American Society of Photogrammetry.

"MPEG Video compression standard, PASSAGE", MPEG Video Compression Standard, Chapman and Hall Digital Multimedia Standards Series, New York, Mitchell, J. L. et al., Chapman and Hall, US, 1996, pp. 21-30.

"Non-Lambertian Shading and Photometric Stereo"—Tagare, et al., SPIE vol. 1260 Sensing and Reconstruction of Three-Dimensional Objects and Scenes (1990).

"Optimal Recovery approach to image interpolation", D. D. Muresan and T.W. Parks, in IEEE Proc. ICIP., vol. 3, 2001 pp. 7-10.

"Picture Coding: A Review", Proceedings if the IEEE ,Netravali A. N. et al., New York, US, vol. 68, No. 3, Mar. 1, 1980, pp. 366-407.

"Robots for the Future"—Shin-ichi, et al. http://jin.jcic.or.jp/nipponaia13/sp05 html. printed Nov. 29, 2001.

"Robust Shape Reconstruction from Combined Shading and Stereo Information"—Lee, et al., SPIE vol. 1771 Applications of Digital Image Processing XV (1992), pp. 171-182.

Search Report for EP 04 01 4906, dated Dec. 27, 2004.

"Shedding Light on Cancer Diagnosis"—Powell (Ed.), May 2000, Laser Focus World.

"Simulation of Images by Photometric Stereo Modeling", Russell, et al., Optical Engineering, Sep. 1991, vol. 30, No. 9, pp. 1337-1345.

Supplementary Partial European Search Report, Mar. 19, 2004.

"The Radio Pill", Rowlands, et al., British Communications and Electronics, Aug. 1960, pp. 598-601.

"Two Image Photometric Stereo Method", Yang et al., SPIE vol. 1826, Intelligent Robots and Computer Vision XI (1992).

Video Camera to "TAKE"13 RF System Lab, Dec. 25, 2001.

Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.

"Wellesley Company Sends Body Montiors into Space"—Crum, Boston Business Journal, 1998.

"Wireless Transmission of a Color Television Moving Image from the Stomach using a Miniature CCD Camera, Light Source and Microwave Transmitter." Swain CP, Gong F, Mills TN. Gastrointest Endosc 1997;45:AB40, vol. 45, No. 4, 1997.

www.jason.net/tinycam.htm, © 2001, printed Dec. 19, 2001.

www.middleeasthealthmag.com/article2.htm—Review proves the value of computers, © 2001, printed Nov. 29, 2001.

www.pedinc.com Personal electronic devices, © 1997.

www.rfnorkia.com—NORIKA3, printed on Jan. 1, 2002.

www.oceanoptics.com—pH Sensor & Accessories © 2001.

* cited by examiner

DEVICE, SYSTEM AND METHOD FOR TRANSFER OF SIGNALS TO A MOVING DEVICE

PRIOR APPLICATION DATA

The present application is a national phase application of International Application PCT/IL03/00834, entitled "Device, system and method for transfer of signals to a moving device" filed on Oct. 15, 2003, which in turn claims priority from U.S. application 60/418,162 filed on Oct. 15, 2002, both of which are incorporated by reference in their entirety.

FIELD OF THE INVENTION

The present invention relates to the transfer of signals, such as for example an energizing signal, to a moving device generally and to such transfer to an in vivo sensing device in particular.

BACKGROUND OF THE INVENTION

Ingestible devices such as capsules known in the art may have an in vivo sensing system, such as an in vivo camera system or other sensing systems such as temperature sensors or pH sensors. An encapsulated in-vivo video camera system may capture and transmit images of the gastrointestinal (GI) tract while it passes through the GI lumen. The system may include a capsule that can pass through the entire digestive tract and operate as an autonomous video endoscope.

FIG. 1 shows an exemplary prior art ingestible device 10 within a human body 12. Device 10 has an imaging device 14, which transmits in vivo images to a set of antennas 16 within an antenna belt 17 surrounding a portion of body 12. Device 10 may, for example, take the form of a capsule, but may take other suitable shapes or forms.

Device 10 has power sources such as batteries 18 which provide power to the various elements of device 10. However, batteries may add weight to the device and may have a limited capacity.

Some endoscopic devices have no batteries. Energy may be provided to these devices by for example transmitting an electromagnetic field at a patient's body in which such a device is inserted. The device may include an element that can receive and convert the transmitted waves to electric power. Typically, a device is an autonomously moving unit where the medium present between the electromagnetic waves receiving unit in the device and the external electromagnetic field may be non-homogenous due to the presence of obstructions or different materials, for example bone, muscle, fat, and tumors. Other material may be present between the receiving unit and the external field. A patient may be placed in an electromagnetic field generating cage and the relevant section of the patient's body may be irradiated by an electromagnetic field in order to ensure that electromagnetic waves reach a device within the patient's body even if obstructions, such as described above, are present. Thus, there exists a need for a more efficient method of providing energy to an in vivo device.

SUMMARY OF THE INVENTION

According to some embodiments of the invention antennas, such as antennas for receiving a signal from an in vivo device, may be operated as a phased array antenna to transfer a signal, for example, an energizing signal, to a moving energy receiving unit containing device, such as an in vivo device. According to embodiments of the invention, an indication used to convey information (typically referred to as a "signal") may be transferred to an autonomous in vivo device. This indication may include, according to one embodiment, an energizing signal, which may typically be used to provide energy to such an in vivo device. Suitable units other than antennas may be used to transfer a signal such as an energy signal.

According to one embodiment there is provided a system for transfer of a signal to an in vivo device, typically an autonomous in vivo transmitting sensing device. According to one embodiment the device includes at least one signal receiving unit. According to an embodiment of the invention the system includes an external phased array antenna. According to one embodiment the phased array antenna includes at least two antennas. Typically the phased array antenna may receive and transmit. According to one embodiment the external phased array antenna can receive a signal from the sensing device and can then transmit to the device phased or arranged in the reverse order to that of receipt of the signal from the sensing device.

According to an embodiment of the invention there is provided a method for transfer of a signal, such as energy, to an autonomous in vivo sensing device. The method may include the steps of for example receiving a signal transmitted from an in vivo device, recording an array or order of receipt, and transmitting a signal to the device using for example the reverse order of receipt of the transmitted signal from the device.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 2B:
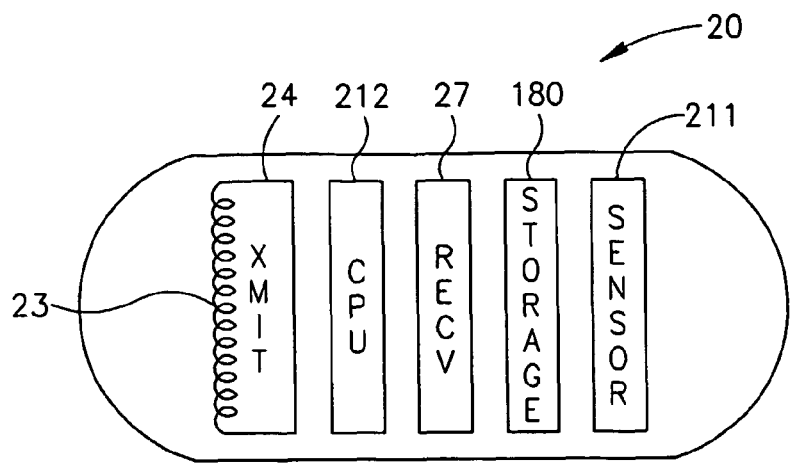
Figure 2B:
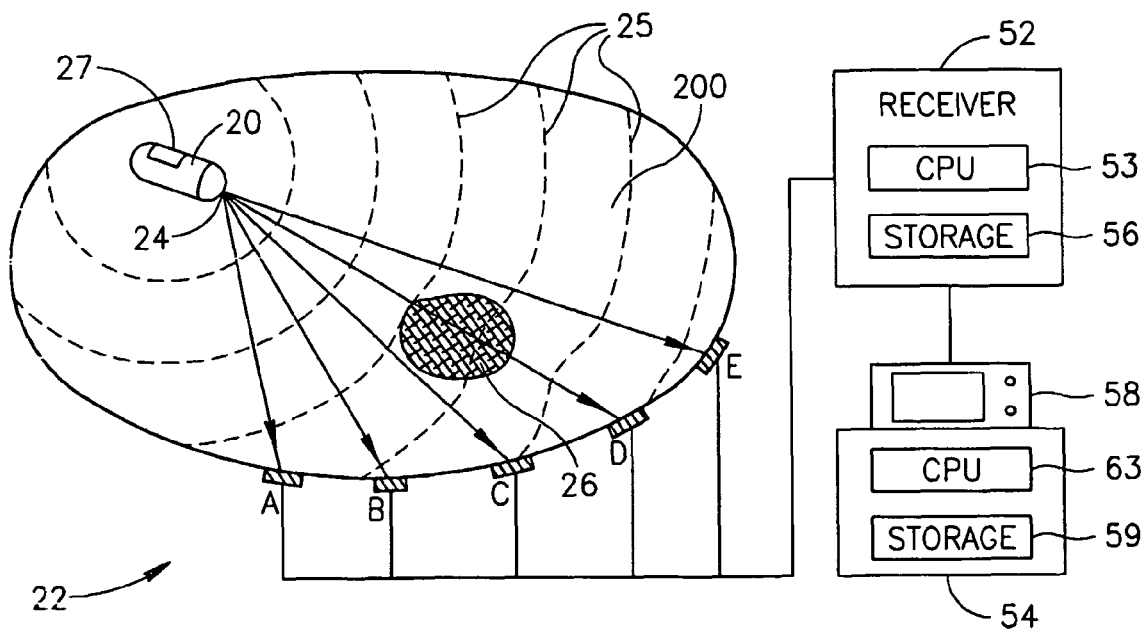
Figure 2B:
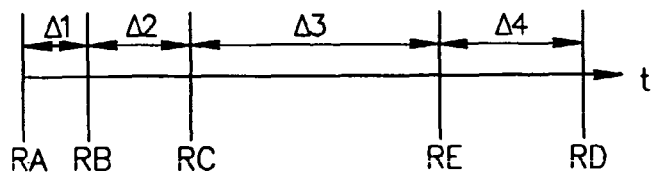
Figure 3A:
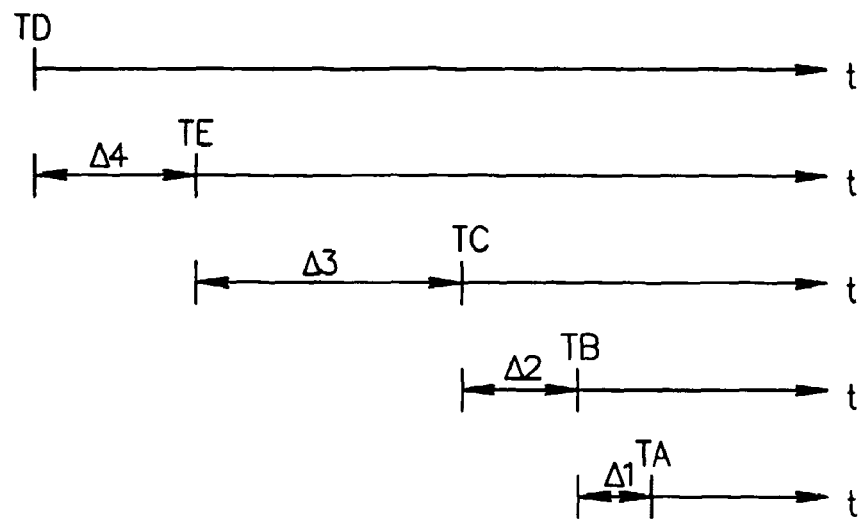
Figure 3B:
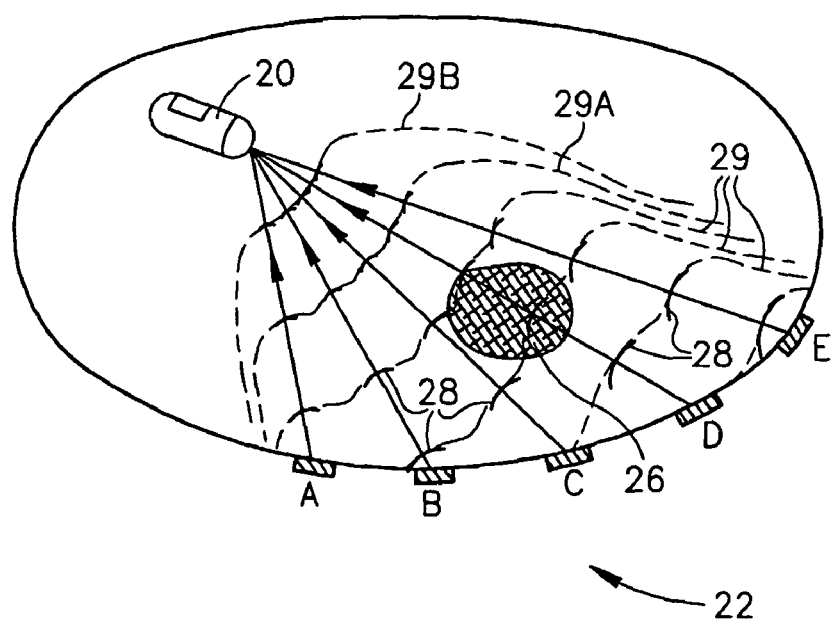
Figure 4A:
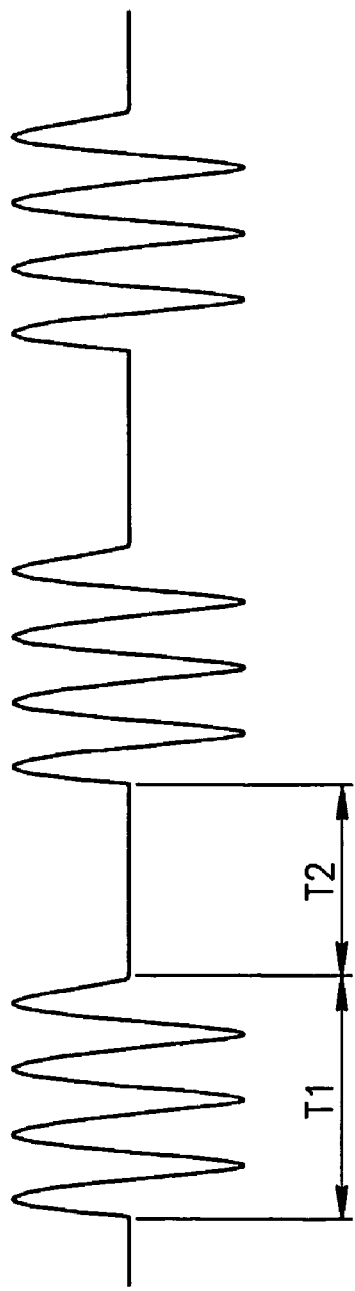
Figure 4B:
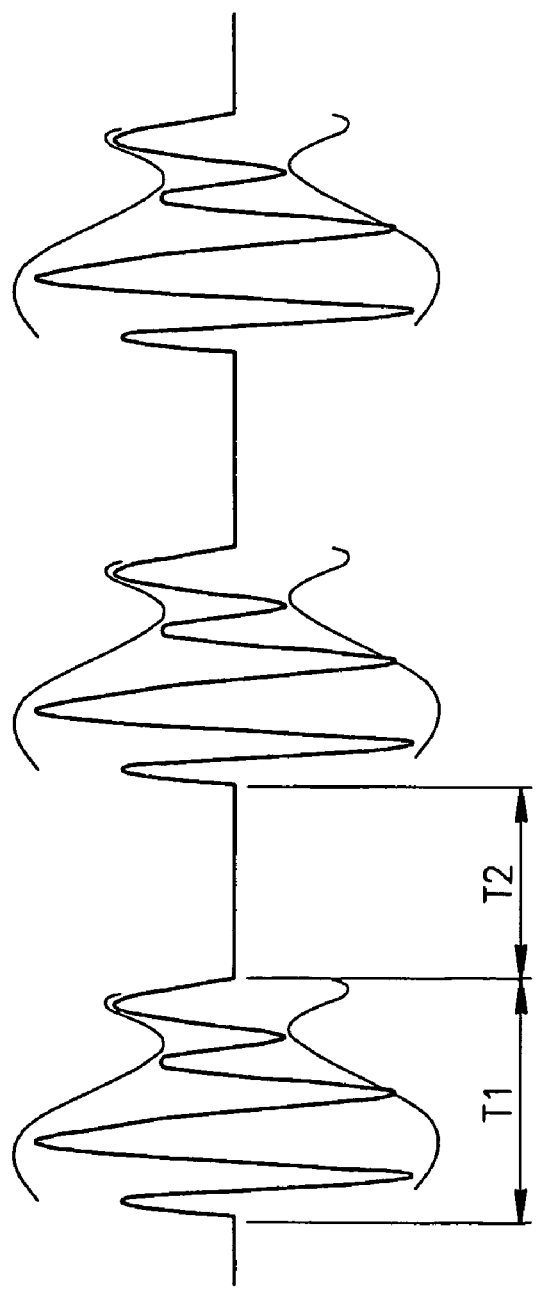
Figure 5:
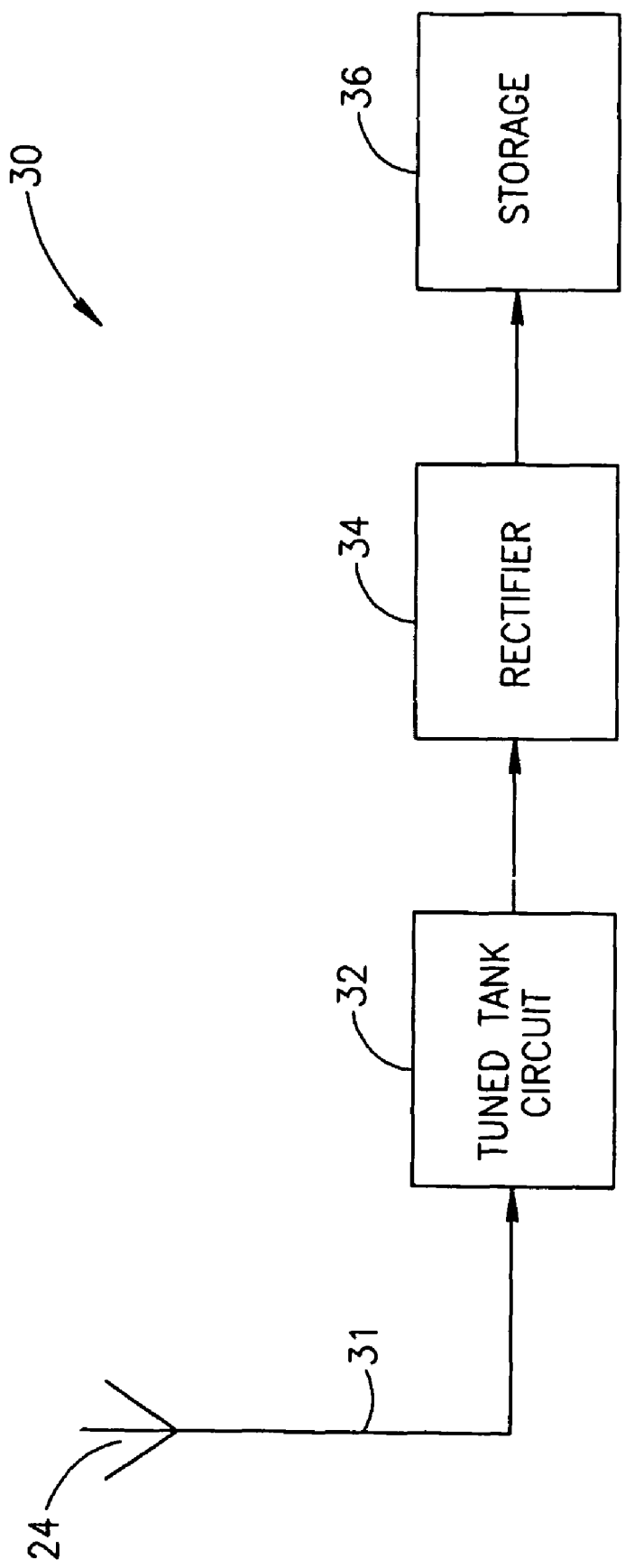
Figure 6:
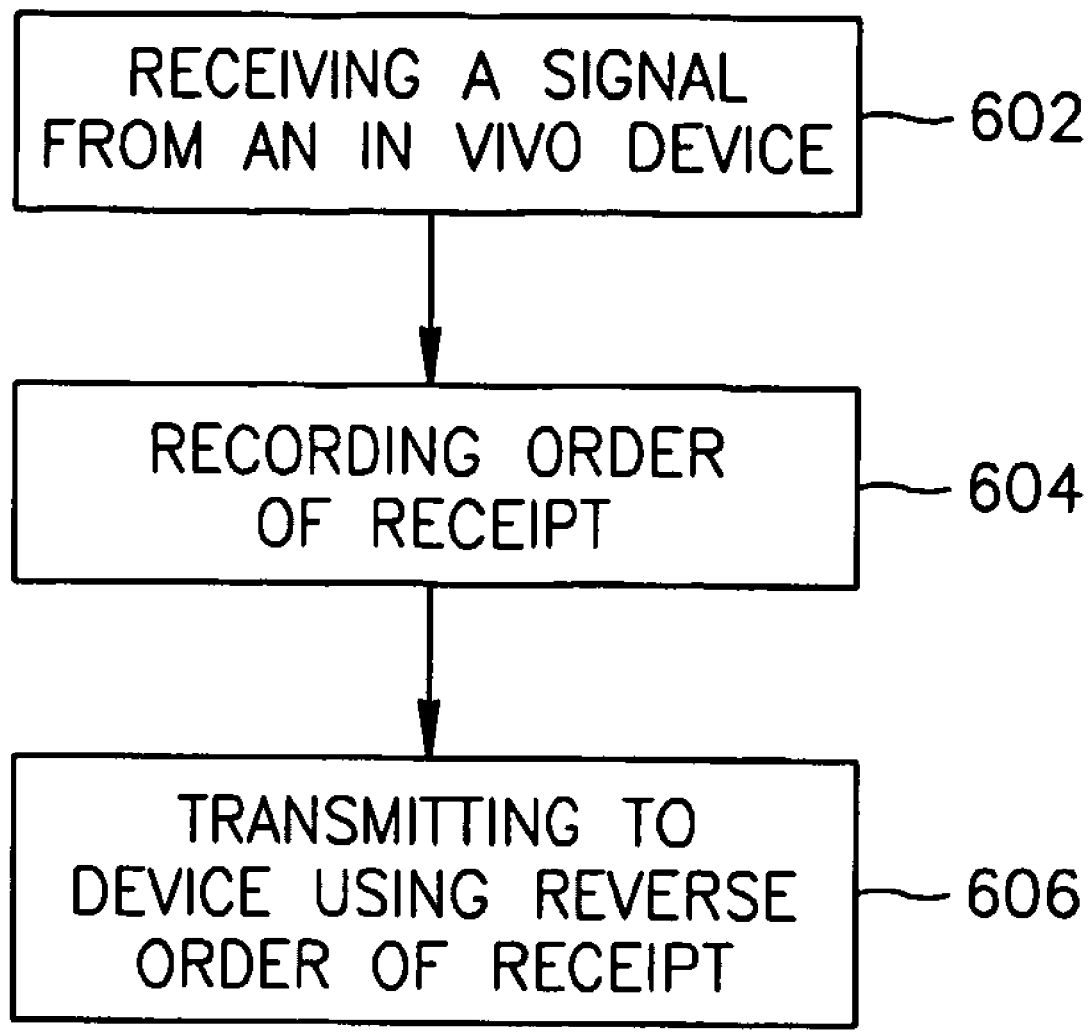

FIGS. $2A_1$ and $2A_2$ are schematic illustrations of a device, constructed and operative in accordance with one embodiment of the present invention; in FIG. $2A_2$, a device is shown transmitting to an antenna, for example an antenna belt;

FIG. 2B is a timing diagram illustration of the receipt of signals to antennas, e.g., the various antennas of FIG. $2A_2$, according to an embodiment of the invention;

FIG. 3A is a timing diagram illustration of the transmission of signals from various antennas, e.g., the antennas of FIG. $2A_2$, in accordance with an embodiment of the present invention;

FIG. 3B is a schematic illustration of the antennas of FIG. $2A_2$ transmitting according to the timing diagram of FIG. 3A, according to an embodiment of the invention;

FIGS. 4A and 4B are graphical illustrations of two alternative signals transmitted to the device, in accordance with an embodiment of the present invention;

FIG. 5 is a block diagram illustration of an energy receiving unit, useful in receiving signals according to embodiments of the invention, e.g., receiving signals of FIGS. 4A and 4B; and FIG. 6 is a flow chart depicting a method for signal transfer to an in vivo device, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Figure 1:
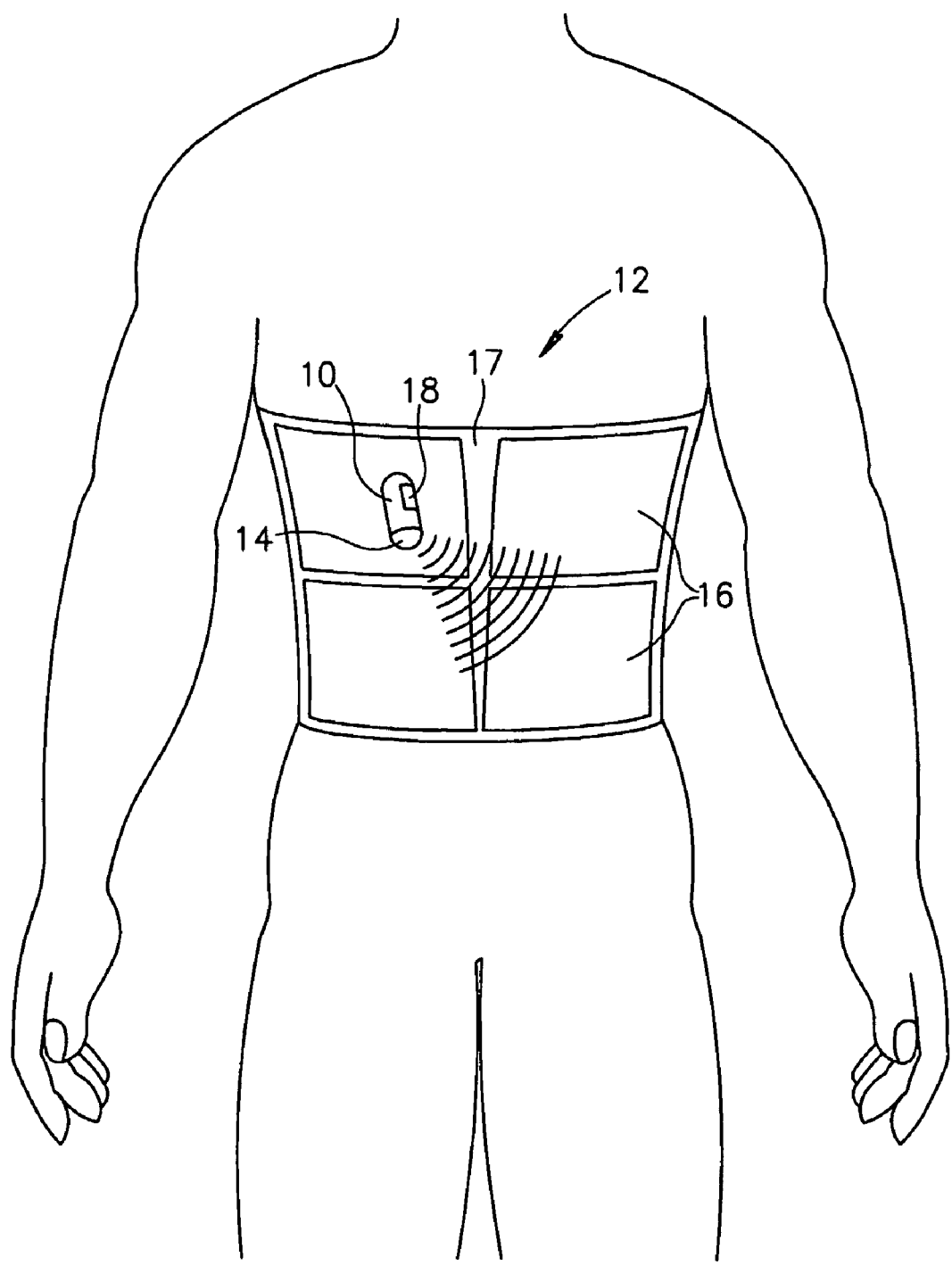
FIG. 1 is a prior art schematic illustration of a system of an ingestible device.

According to some embodiments of the invention antennas in for example a garment or holder such as an antenna belt (for example, antenna belt 17 of FIG. 1) may in one embodiment be operated as a phased array antenna. Example of phased array antennas are discussed, for example, in the book, *Electromagnetics with Applications*, $5^{th}$ Edition, by Kraus and Fleisch, McGraw-Hill, 1999, pp. 264-273. Antennas may be arranged in other fashions, using other holders or garments, and a holder need not be used.

As is known in the art, phased array antennas may generate focused beams which may be moved (e.g., by changing the relative phasing of the antennas), for example as the object receiving the beam moves. According to an embodiment of the invention such a beam may be used to transfer energy or any other suitable signal to a moving receiving unit (e.g., an energy receiving unit), such as a unit in an in vivo device.

In one embodiment, in contrast to some prior art phased array antennas, which require knowing the location of an object to which a signal is being transmitted and require a homogenous medium through which to transmit, a signal from an in vivo device may for example provide enough information for a phased array to focus a beam back to the device without requiring knowledge of the location of the device or of the intervening medium. In other embodiments location information may be known or calculated.

Reference is now made to FIGS. $2A_1$, $2A_2$, 2B, 3A and 3B which illustrate an embodiment of the present invention. FIGS. $2A_1$, $2A_2$ and 3B show an in vivo sensing device, such as an ingestible imaging device 20 (which may, for example, take the form of a capsule, but may take other suitable shapes or forms) with a receiving unit 27, such as an energy receiving unit and an antenna array 22, while FIGS. 2B and 3A are timing diagrams of the operations of the device and the antenna array, respectively, according to embodiments of the invention. Other suitable antenna arrangements and timing schemes may be used. Receiving unit 27 may receive signals other than, for example, energy.

In FIG. $2A_1$, according to one embodiment of the invention, device 20 includes a sensing system 211, a signal receiving unit, such as receiving unit 27, a transmitter 24, one or more antennas 23, and a processing unit 212. In alternate embodiments, the sensing device need not be a capsule or a self contained or autonomous device. For example, the sensing device may be or may be located at the tip of a medical device, such as, an endoscope, needle, catheter, stent etc.

The sensing system may include a suitable in vivo sensor, such as a pH meter, a temperature sensor, a pressure sensor, a biological or chemical sensor, an image sensor, etc. More than one sensor may be included in a device according to some embodiments. The in vivo sensor may be exposed to the in vivo environment by, for example, being properly positioned in the device 20. For example, a pH sensor may include an electrode which protrudes from the shell or covering of the device, such as the capsule shell, as is known in the art. In another embodiment an image sensor may be exposed to the in vivo environment through an optical window in the device 20, as known in the art. Typically, the in vivo sensor relays data to a transmitter 24 for transmitting the data to an external receiving system, such as to antenna array 22. An in vivo imaging device which transmits image data to an external receiving system is described, for example, in embodiments described in U.S. Pat. No. 5,604,531 to Iddan, et al. and/or WO 01/65995 to Glukhovsky, both assigned to the assignee of the present application and both incorporated by reference. An external receiving, processing and display system which may be used with embodiments of the present invention may be similar to embodiments described in U.S. Pat. No. 5,604,531 to Iddan, et al. and/or WO 01/65995 to Glukhovsky. Of course, other suitable in-vivo sensing systems and external receiving, processing and display systems may be used.

According to some embodiments, an imaging device such as a capsule shaped device is inserted into a body lumen such as, for example, the gastrointestinal tract. For example, the device may be ingested. According to one embodiment the device 20 typically includes an imaging sensor (e.g., sensing unit 211), an illumination source (not shown) and an optical head (not shown) which may include one or more optical elements, such as one or more lenses and a lens holder. One or more suitable optical elements may be used for focusing images onto the imaging sensor. The optical head may be placed behind an optical window or dome to, for example, isolate its electric components from liquids found in a body, which may interfere with the operation of such components. The imaging sensor may be, for example, a solid state imaging sensor, such as charged coupled devices (CCDs) and complementary metal oxide semiconductors (CMOS). The imaging sensor may generate electronic signals such as image signals, which may be transmitted by way of, for example, a circuit board to a processor chip, which may, inter alia, carry out processing or conditioning of the signal. An example of a processor chip that may be used in embodiments of the present invention is an ASIC (application specific integrated circuit). According to one embodiment the ASIC may have transmitting capabilities, for example, operating on a minimum shift keying (MSK) modulation system to effect transmitting of digital signals through an antenna on radio frequencies to a receiving system. Thus, in certain embodiments components such as transmitter 24 may be combined with other components, e.g., with processing unit 212. Other components and other arrangements of components may be used.

According to some embodiments transmitter 24 may be capable of working in a receiving and in a transmitting mode for transmitting signals to, for example, an external phased array antenna 22 and for receiving signals from antenna 22. For example, transmitter 24 may be a transceiver. According to some embodiments transmitter 24 may include or be attached to an omni-directional antenna; for example antenna 23 may be an omni-directional antenna. According to some embodiments antenna 23 may include more than one antenna. According to some embodiments transmitter 24 is capable of transmitting to an external phased array antenna 22 while receiving unit 27 is capable of receiving signals transmitted from the antenna 22. Other components may be used for transmitting and receiving.

According to some embodiments a power supply, such as one or more batteries, is included in the device 20 for providing energy to elements of the device. According to some embodiments an energy storage unit 180 may be included in the device 20. The storage unit 180 may include, for example, a rechargeable battery, a capacitor or other suitable chargeable units. Typically a storage unit 180 is connected to receiving unit 27, possibly via intermediate components. According to some embodiments these two units may be contained in the same component. According to some embodiments receiving unit 27 may provide energy to at least some of the device elements (e.g., to an illumination source, to an image sensor, etc.)

In FIG. $2A_2$ device 20 transmits a signal to antenna array 22 using, for example, an omni-directional antenna, for example antenna 23. Antenna array 22 typically includes two or more antennas. In FIG. $2A_2$ antenna array 22 includes antennas A, B, C, D and E, however any other suitable number of antennas may be used. Each of the antennas A, B, C, D and E may be omni-directional, but other types of antennas may be used. According to embodiments of the invention, the antennas may operate in receiving and/or in transmitting modes. For example, antenna array 22 may include transceivers. According to some embodiments antenna array 22 may be designed to surround a body portion. The array may be included in a garment that can be worn or placed on a relevant body portion, e.g., around a patient's stomach.

Typically, located outside the patient's body in one or more locations, are a receiver 52, connected to antennas A-E, for receiving image and possibly other data from device 20, a receiver storage unit 56, for storing image and other data, and a processor or controller 53. The receiver 52 may be connected (permanently or temporarily) to, for example, a data processor 54, a data processor storage unit 59, and an data or image monitor 58, for displaying, for example, image data transmitted by the device 20 and received and/or recorded by the receiver 52. Typically, the receiver 52 and receiver storage unit 56 are small and portable, and are worn on the patient's body during recording of the images. Preferably, data processor 54, data processor storage unit 59 and monitor 58 are part of a personal computer or workstation, which includes standard components such as a controller or processor 63, a memory (e.g., storage unit 59, or other memory), a disk drive, and input-output devices, although alternate configurations are possible. In alternate embodiments, the data reception and storage components may be of another configuration.

The receiving and recording components may be, for example, similar to embodiments described in the above-mentioned U.S. Pat. No. 5,604,531 and/or WO 01/65995. However, the receiving and recording components may be of other configurations.

The signal transmitted from device 20 may be any type of signal, such as a signal including data (e.g., image data, pH data, etc.), an image signal, an audio signal, a synchronization signal, a localization signal, a signal from one or more sensors in the device that send signals (such a PH, temperature, pressure) and/or chemical and/or biological signals from an appropriate sensor that may be included in the device, etc. According to one embodiment an external receiving system (e.g., receiving system 52), which may include antenna array 22, may further include or be attached to a control and/or processing unit (e.g., data processor 54, controller or processor 63, controller or processor 53) for executing processing operations, for example, as described herein. Other components, such as a memory, may be included in the external receiving system.

FIG. $2A_2$ shows an exemplary signal, propagating as a wave through a patient's body to antenna array 22. The wave is shown with constant phase surfaces 25 that are shown roughly circular and which bend, for example, as they go through an obstruction 26 (such as a body part). It should be appreciated that this is a simplification for illustrative purposes; typically, the shape of the wave is a function of the media through which the wave passes, its homogeneity, as well as the size and shape of the obstruction(s).

In the example of FIG. $2A_2$, the medium 200 may be relatively homogeneous but device 20 may not be centered relatively to antenna array 22. It is fairly distant from antennas A, B, C, D and E and on the opposite side therefrom of obstruction 26. Accordingly, antennas A, B, C, D and E may receive the signal at different times. Antenna A is the closest antenna to device 20 and antenna E is the furthest antenna. Antenna D has an obstructed "line-of-sight" to device 20 due to the presence of obstruction 26.

The signal in this example may arrive at the antennas in the following order: antenna A, antenna B, antenna C, antenna E and antenna D, wherein, for each neighboring antenna pair, there is a time difference array of arrival, for example, as shown in FIG. 2B. Thus, between antennas A and B, the time difference is $\Delta 1$, that between antennas B and C is $\Delta 2$, that between antennas C and E is $\Delta 3$ and that between antennas E and D is $\Delta 4$. This arrangement and operation is by way of example only; in use, other operational situations may arise.

As part of the processing operation, the strength array, typically defined as the strength of the signal at each antenna as well as the time array, typically defined as the timing of receipt of the signal at each antenna, may be stored. With this information, for example, the signal may be typically processed, using the signal from the antenna with the strongest signal and ignoring the output of the remaining signals. Other suitable systems and methods for storing signal receipt data may be used or stored. For example, separate data constructs or structures for timing and strength need not be used, and other suitable data, other than timing and strength, may be used.

According to an embodiment of the invention a "time array" may describe how a signal traveled from device 20 to antenna array 22 and further, that transmitting a signal to device 20 using the antennas of array 22 phased with the reverse timing to that of the receipt of the signal from device 20 may generate a focused beam back to device 20. This is shown for example in FIGS. 3A and 3B.

Thus, the phasing for the example of FIGS. $2A_2$ and 2B, which is shown in FIG. 3A, is to activate the antennas in the following order, reverse to that of receipt: antenna D, antenna E, antenna C, antenna B and antenna A and to define their phasing as the reverse phasing of receipt, as follows: $\Delta 4$, $\Delta 3$, $\Delta 2$, and $\Delta 1$.

FIG. 3B shows, as an example, the signals from the five antennas A, B, C, D and E. Each antenna may produce its own omni-directional wave 28, timed according to, for example, the phasing discussed above. The interference of these waves may produce a wave front pattern, for example waves 29 that may converge into a focused beam according to for example the Huygens principle known in the art In this example, antenna D may transmit first. Its wave may be shown ahead of the others but may be slowed down as it passes through obstruction 26. Those of its waves which have passed through obstruction 26, for example, have almost converged at wave 29A, with those of the other antennas and are closer to converging, for example at wave 29B, and generally may converge upon arrival at device 20. Control of transmission may be performed by a suitable control unit, for example, e.g., data processor 54, controller or processor 63, and/or controller or processor 53.

Similarly, the waves produced by the other antennas begin as separate waves but, due to the phasing of production of the waves, converge generally upon arrival at device 20.

With a focused beam according to an embodiment of the invention, the amount of energy transmitted from antenna array 22 may be approximately one order of magnitude lower than the amount transmitted from an omni-directional or prior art antenna for device 20 to capture the same amount of energy. In other words, the phased array, according to an embodiment of the invention, reduces the amount of power needed for transmission by a factor of at least 10, for example, depending on the number of antennas used. Typically, a larger amount of antennas facilitates focusing of a transmitted beam. In other embodiments, other reductions in the amount of power needed may be achieved.

The focused beam may transmit sufficient energy to energize an energy receiving unit in device 20. An exemplary energy receiving unit 30 is shown in FIG. 5. According to one embodiment of the invention, device 20 may have no batteries or possibly, much smaller ones or fewer batteries than devices of the prior art. According to embodiments of the invention a device may have a storage unit, e.g., a capacitor or one or more rechargeable batteries, e.g., for storing energy transmitted from an antenna array 22. For example, storage unit 180 may store energy.

FIGS. 4A and 4B, to which reference is now made, illustrate two alternative energizing signals, according to embodiments of the invention. Suitable energizing signals other than those shown in FIGS. 4A and 4B may be used. FIG. 4A shows a simple harmonic train having active portions T1 and silent intervals T2 between pairs of active portions T1. FIG. 4B shows an amplitude modulated version of the energizing signal of FIG. 4A. Any suitable type of modulation known in the art (two well-known examples of which are amplitude modulation (AM) or frequency modulation (FM)) may be utilized and the modulation may be used to encode uplink data and/or commands to device 20.

During silent intervals T2, antenna array 22 may be in "receive mode", ready to receive any signal which device 20 may transmit. Such signals typically include data that device 20 has acquired, such as images, biological data, chemical data, etc. Other signals may be transmitted, such as beacon signals or other signals. In one embodiment silent intervals T2 are of the order of for example 1 msec or of any length sufficient to receive a typical transmission from device 20. Other intervals may be used.

Silent intervals T2 may be of a fixed length or may be variable, ending once a transmission from device 20 has ended. Fixed length intervals may indicate a synchronous operation while variable length transmissions may indicate an asynchronous operation. Active portions T1 may start only after a first transmission may be received from device 20. Device 20 may switch its antenna 23 from transmit mode to receive mode once it has finished its transmission and may switch back to transmit mode once active portion T1 has been received. Similarly, antenna array 22 may switch back to receive mode once it has finished transmitting active portion T1. Other suitable configurations and signaling schemes may be used.

Active portions T1 may be, for example, radio frequency (RF) bursts of about 1 millijoule of energy with a frequency of up to, for example, 1.0 GigaHertz. Since the energizing signals of FIGS. 4A and 4B are transmitted as focused beams, the energy may be efficiently transferred to device 20, to be captured by energy receiving unit 27. Other suitable energy levels and frequencies may be used; the values discussed herein are only by way of example.

Reference is now made to FIG. 5. In one embodiment, energy receiving unit 30 may include components such as a duplexer switch 31, a tuned tank circuit 32, a rectifier 34 and an energy storage unit 36. If present, switch 31 may connect energy receiving unit 30 to antenna 23 during receive mode. Other ways of determining between transmission and reception may be used. For example, two separate frequencies may be used, in which case, there may be no need for switch 31. Other suitable configurations for an energy receiving unit may be used.

Tuned tank circuit 32 may be any suitable circuit that may tune to the carrier frequency of active portions T1. Tank circuits are known in the art and are described, for example, in *The Art of Electronics*, $2^{nd}$ Edition, by Horowitz and Hill, Cambridge University Press, 1989, p. 883. Accordingly, they will not be described further herein except to indicate that they are minimally an "LC" block formed of a capacitor and an inductor.

Rectifier 34 may be, for example, a diode bridge and may, for example, rectify the sinusoidal energizing signal produced by tank circuit 32, thereby producing a non-negative energizing signal having a large portion of the power of the signal transmitted from antenna array 20. According to one embodiment energy storage unit 36 may be a capacitor or a rechargeable battery pack and may be operative to receive the non-negative energizing signal of rectifier 34. Other components and methods may be used.

It will be appreciated that, with regular transmissions of active portion T1, energy storage unit 36 may be fairly small.

It will be appreciated that the present invention may be utilized in many systems that have a multitude of receiving antennas and a mobile device (e.g., a mobile phone) moving through the area covered by the receiving antennas.

For example, if an in vivo device (e.g., implantable lab on chip, in vivo sensing device, such as an imaging device, stimulating device, RF ID tag etc.), includes a transmitter, then the transmitter and the antennas receiving its energizing signal may perform the energy transfer method according to an embodiment of the invention. Accordingly, such devices within the body may require no or relatively small energy storage units. Furthermore, a patient may be subject to a smaller electromagnetic field, rendering the method device and system according to embodiments of the invention more efficient than known methods and devices.

It will further be appreciated that, according to an embodiment of the present invention, sufficient energy may be transferred to, for example, cauterize or destroy a tumor or otherwise provide in vivo treatment. According to one embodiment, an in vivo device may identify the presence of a pathology, such as a tumor, and transmit a signal indicating such. With this signal, in accordance with an embodiment of the invention, a strong, focused beam may be provided back to the location of the device, or slightly moved there from, resulting in energy focused (e.g., to burn, cauterize etc.) at the location of the tumor.

It will still further be appreciated that embodiments of the present invention may be used in typically non-biomedical applications and, in particular, in any powered device that is difficult to access. Embodiments of the present invention may be used for example to power mobile telephones. The battery of the device need not be replaced; instead, the powered device may have a transmitter thereon transmitting a sufficient signal that may allow the antenna array to then transmit back an energizing signal in the from, for example, a focused beam with sufficient energy to store until the next transmission from the powered device.

A system and method according to another embodiment may be applied to an RF identification (ID) tag. RF ID tags may provide identification or other information, for example when queried, and may be passive, providing a signal only when queried, or active, periodically or otherwise providing a signal. RF ID systems may utilize various methods to identify the location of each tag. One standard localization method that may be used, for example, is through triangulation.

RF ID tags may be utilized in numerous in vivo applications; for example, an RF ID tag may be included in an ingestible device such as a capsule. The presence of the RF ID tag in a patient's body at different periods after ingesting it may give a picture of the patient's gastrointestinal motility. Thus, a patient's body may be scanned by a system, according to an embodiment of the invention, for the presence of a tag and for providing energy to such a tag.

The present invention, according to one embodiment, may be utilized with active tags, providing the tags with periodic bursts of an energizing signal after receiving one of the periodic signals from the tags. Additionally, the present invention may be utilized with RF ID tags operating at low power. Such a tag may be one whose battery life is almost finished. Since a low power signal is noisy, the system may require multiple transmissions before being able to generate the focused beam. Alternatively, the system may provide a single, omni-directional pulse to provide sufficient energy to the tag for it to provide a relatively non-noisy signal. The antenna array may then determine the phasing from this relatively non-noisy signal and may generate a focused beam back to the tag, thereby to increase its stored energy.

Reference is now made to FIG. 6 in which a schematic flowchart of a method for transfer of a signal to an in vivo sensing device, is depicted. In a first step a signal is received form an in vivo sensing device (602). Typically, the signal is received by an external phased array antenna. An array or order of receipt is recorded (604) (and may be stored, for example in storage unit 59 and/or storage unit 56) and a signal is transmitted to the in vivo device using the reverse order of receipt of the transmitted signal from the device (606). Recording of received signals, calculation of a response signal, and control of transmission may be performed by a suitable control unit, for example, e.g., data processor 54, controller or processor 63, and/or controller or processor 53. The array or order of receipt may be for example, a time array or a strength array of receipt, or other suitable array. According to one embodiment the method includes the step of energizing at least one component of the device.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A system for transferring an energizing signal to an in-vivo device, said system comprising:
   an in-vivo sensing device, the in-vivo device comprising a signal transmitter configured to transmit a first signal, an energy storage unit, and a signal receiving unit for receiving a second signal for being stored in the energy storage unit; and
   an external phased array antenna, the phased array antenna comprising two or more antennas for receiving the first signal in a reception order according to reception time (s),
   wherein the two or more antennas are configured to transmit the second signal in a reversed order of the reception order of the first signal, such that the time difference between transmission of the second signal through a first antenna of the two or more antennas and transmission of the second signal through a second antenna of the two or more antennas equals to the time difference between the reception times of the first signal at the first antenna and the second antenna.

2. The system according to claim 1 wherein the phased array antenna is configured for surrounding a portion of a body.

3. The system according to claim 1 wherein the sensing device includes an image sensor.

4. The system according to claim 1 wherein the sensing device comprises a capacitor or a rechargeable battery.

5. The system according to claim 1 wherein the sensing device comprises at least one antenna.

6. The system according to claim 1 wherein the phased array antenna is configured to transmit a signal having an active portion and a silent interval.

7. The system according to claim 6 wherein the silent interval lasts for a period in the order of magnitude of 1 msec.

8. The system according to claim 6 wherein the active portion includes RF bursts.

9. The system according to claim 6 wherein the active portion includes bursts of about 1 milijoule.

10. The system according to claim 6 wherein the active portion includes bursts at a frequency of about 1 GigaHertz.

11. The system according to claim 1 wherein the phased array antenna is configured to transmit a modulated signal.

12. A method for transferring an energizing signal to an in vivo device, the method comprising the steps of:
   receiving a first signal transmitted from said in vivo device by a phased array antenna comprising two or more antennas;
   recording a reception order according to reception time of said first signal through the phased array antenna; and
   transmitting, by said phased array antenna, a second signal to said in vivo sensing device in a reverse order, such that the time difference between transmission of the second signal through a first antenna of the two of more antennas and transmission of the second signal through a second antenna of the two of more antennas equals to the time difference between the reception times of the first signal at the first antenna and the second antenna.

13. The method according to claim 12 wherein the order of receipt is a time array.

14. The method according to claim 12 comprising the steps of energizing at least one component of said in vivo sensing device.

15. The method according to claim 12 comprising the steps of:
   transmitting a signal from the in vivo sensing device;
   switching from transmit to receive mode;
   receiving a signal which includes at least one active portion and at least one silent interval; and
   switching from receive mode to transfer mode at an end of the active portion of the signal.

16. The system according to claim 1, wherein the signal transmitter comprises an RF ID tag.

17. The system according to claim 16, wherein the RF ID tag is adapted to transmit said first signal.

18. The system according to claim 5, wherein at least one of said at least two antennas is an omni-directional antenna.

* * * * *